United States Patent
Flore et al.

(10) Patent No.: US 6,280,745 B1
(45) Date of Patent: Aug. 28, 2001

(54) METHODS AND COMPOSITIONS FOR THE DELIVERY OF PHARMACEUTICAL AGENTS AND/OR THE PREVENTION OF ADHESIONS

(75) Inventors: Stephen G. Flore, San Diego; Luis A. Dellamary, San Marcos, both of CA (US); Lorraine E. Reeve, Dexter, MI (US); Jeffry G. Weers, Half Moon Bay, CA (US)

(73) Assignee: Alliance Pharmaceutical Corp., San Diego, CA (US)

( * ) Notice: Subject to any disclaimer, the term of this patent is extended or adjusted under 35 U.S.C. 154(b) by 0 days.

(21) Appl. No.: 09/582,508

(22) PCT Filed: Dec. 23, 1997

(86) PCT No.: PCT/US97/23865

§ 371 Date: Aug. 22, 2000

§ 102(e) Date: Aug. 22, 2000

(87) PCT Pub. No.: WO99/32151

PCT Pub. Date: Jul. 1, 1999

(51) Int. Cl.[7] .......................... A61K 9/00; A61K 31/765; A61K 31/74; A61F 2/00
(52) U.S. Cl. .......................... 424/400; 424/486; 424/423; 424/78.37; 424/487; 424/488; 424/484
(58) Field of Search ...................... 424/400, 486, 424/423, 488, 484, 487, 78.37; 514/944

(56) References Cited

U.S. PATENT DOCUMENTS

| | | |
|---|---|---|
| 2,674,619 | 4/1954 | Lundsted . |
| 2,677,700 | 5/1954 | Jackson et al. . |
| 2,979,528 | 4/1961 | Lundsted . |
| 3,036,118 | 5/1962 | Jackson et al. . |
| 3,535,307 | 10/1970 | Moss et al. . |
| 3,829,506 | 8/1974 | Schmolka et al. . |
| 4,188,373 | 2/1980 | Krezanoski . |
| 4,474,751 | 10/1984 | Haslam et al. . |
| 4,474,752 | 10/1984 | Haslam et al. . |
| 4,474,753 | 10/1984 | Haslam et al. . |
| 4,478,822 | 10/1984 | Haslam et al. . |
| 4,810,503 | 3/1989 | Carson et al. ...................... 424/76.3 |
| 5,126,141 | 6/1992 | Henry ................................... 424/423 |
| 5,366,735 | 11/1994 | Henry ................................... 424/426 |
| 5,582,837 | 12/1996 | Shell . |
| 5,651,985 | 7/1997 | Penners et al. . |
| 5,908,612 | * 6/1999 | Dailey et al. .......................... 424/49 |

FOREIGN PATENT DOCUMENTS

| | | |
|---|---|---|
| 0419156A2 | 3/1991 | (EP) . |
| 0470251A1 | 2/1992 | (EP) . |
| 0551626A1 | 7/1993 | (EP) .............................. A61K/47/10 |
| WO 90/04971 | 5/1990 | (WO) .............................. A61K/33/34 |
| WO 91/19481 | 12/1991 | (WO) .............................. A61K/9/107 |
| 9747285 | 12/1997 | (WO) . |
| 9811879 | 3/1998 | (WO) . |

OTHER PUBLICATIONS

Holtz et al. Effect of Thirty-Two Per Cent Dextran 70 On Peritoneal Adhesion Formation and Re-Formation After Lysis 6 Fertiltiy & Sterility V.33 660–662 (Jun. 1980).

Oelsner et al. Chondroitin Sulphate A New Intraperitoneal Treatment for Postoperative Adhesion Prevention in Rabbit 11 J. Reprod. Med. V 32 812–814 (Nov. 1987).

* cited by examiner

Primary Examiner—Thurman K. Page
Assistant Examiner—Blessing Fubara

(57) ABSTRACT

The present invention provides a composition comprising one or more constitutive polymers and modifier polymers and/or hydrophilic co-surfactants useful for reducing adhesions or delivering bioactive agents. Methods for preventing and/or reducing post-surgical adhesions or delivering bioactive agents are provided.

28 Claims, 4 Drawing Sheets

METHODS AND COMPOSITIONS FOR THE DELIVERY OF PHARMACEUTICAL AGENTS AND/OR THE PREVENTION OF ADHESIONS

This application is the national phase of international application PCT/US97/23865 filed Dec. 23, 1997 which designated the U.S.

FIELD OF THE INVENTION

The present invention generally relates to pharmaceutical preparations and methods of their use. More particularly, the present invention relates to preparations suitable for the reduction of adhesion formation in mammals or the delivery of pharmaceutically active compounds.

BACKGROUND OF THE INVENTION

Over the years, methods have been developed to achieve the efficient delivery of therapeutic or diagnostic agents to a mammal requiring such treatment. Aqueous liquids which can be applied at room temperature in a free flowing state but which forms a semi-solid gel when warmed to body temperature have been used in such capacities for some time. Such systems combine ease of application with greater retention at the site of application than the use of exclusively free flowing vehicles. For example, in U.S. Pat. No. 4,188,373, incorporated herein by reference, Pluronic® polyols are used in aqueous compositions to provide thermally gelling aqueous systems. Adjusting the concentration provides the desired sol-gel transition temperature. More particularly, the lower the concentration of the incorporated polymer the higher the sol-gel transition temperature. At a critical polymer concentration minimum, the system reaches a point where a gel will not form at any physiologically compatible temperature. While such vehicles are a substantial improvement over prior art systems, it is hard to precisely adjust the sol-gel temperature to the desired value.

In U.S. Pat. Nos. 4,474,751; '752; '753; and 4,478,822, each incorporated herein by reference, drug delivery systems are described which utilize thermosetting gels. In these systems both the gel transition temperature and/or rigidity of the gel may be modified by adjustment of the pH and/or the ionic strength as well as by the concentration of the polymer. Although such vehicles may be efficiently used for the delivery of bioactive agents, establishment and maintenance of the desired sol-gel temperature and/ or persistence of the gel may be complicated by several variables including the localized physiology of the mammalian subject. Accordingly, a need still exists for pharmaceutical preparations or drug delivery compositions that allow for the establishment of a precise sol-gel transition temperature and accurate control of the gel dissolution rate in vivo.

Control of such characteristics is also desirable when similar polymeric gels are used for the prevention of adhesion formations in mammals. Adhesions are thought to form following a trauma or injury to the peritoneum. This results in increased vascular permeability, which produces an inflammatory exudate and results in the formation of a fibrin matrix. In normal wound healing, the fibrin matrix is removed by fibrinolysis, and subsequent fibroblast proliferation results in remesothelialization. However under the ischemic conditions present following surgical trauma the fibrinolytic process is suppressed and the fibrin matrix may persist. If it persists until about day three, significant collagen deposition within the fibrin matrix, can lead to adhesion formation.

As will be appreciated by those skilled in the art, prevention of adhesions has been the subject of various efforts since the beginning of this century (see, for example, *Surgery, Gynecology and Obstetrics,* 133:497–509, 502–503 (1971)). These efforts have included means of preventing the fibrin-coated walls of the intestine from contacting one another by distending the abdomen with oxygen or filling the abdomen with various liquids such as saline solution, paraffin, olive oil, lanolin, concentrated dextrose solution, various macromolecular solutions and silicones.

High molecular weight dextran either alone or in combination with dextrose has also been used (Holtz, et al., *Fertility and Sterility,* 33:660–662 (1980); 34:394–395 (1980)). One such formulation, HYSKON® (Pharmacia, Piscataway, N.J.), which comprises 32% aqueous solution of dextran 70 containing 10% dextrose, was effective in reducing peritoneal adhesions subsequent to surgery. However, it has been reported that HYSKON has a tendency to support bacterial proliferation. Further concern has been expressed over the anaphylactoid potential of dextran (DiZerega et al., *Fertility and Sterility,* 40:612–619 (1983)). In addition, the benefit of dextran 70 in preventing post-operative adhesions was shown to be limited to the more dependent regions of the pelvis.

The use of resorbable fibrous barriers to separate injured tissues has also been described (Linsky, *J. Reprod. Med.,* 17–20 (1987)). For example, TC-7 (Johnson and Johnson Products, Inc., New Brunswick, N.J.), an oxidized cellulose fabric barrier, has been used as a treatment to prevent organ adhesion to the peritoneum. Other solid sheet devices include polytetrafluoroethylene (Gore-Tex®, W. L. Gore) and crosslinked hyaluronic acid (Seprafilm®Genzyme Corp.).

Chondroitin sulfate and sodium carboxymethyl cellulose have also been used to prevent the formation of postoperative adhesions in the rabbit uterus (Oelsner et al., *J. Reprod. Med.* 32:812–814 (1987)). Chondroitin sulfate solutions have also been proposed for intraperitoneal use in the prevention of adhesions in rabbits.

More recently, aqueous gel compositions comprising polyalkylene polymers have been shown to successfully reduce adhesions (U.S. Pat. No. 5,366,735, incorporated herein by reference). These compositions can be applied below room temperature as a liquid and form semi-solid gels when warmed to body temperature. However, as with the aforementioned drug delivery compositions, precise control of the sol-gel transition temperature and dissolution rate of the gel within the physiological environment still present problems in many cases. Accordingly, despite these previous efforts, a need exists for improved means to treating and/or preventing post-surgical adhesions.

As such, it is an object of the present invention to provide polymeric gel compositions which allow for precise control of the sol-gel transition temperature and/or dissolution rate of the gel once formed.

It is a further objective of the present invention to provide gelling drug delivery preparations, and methods for their use, comprising at least one bioactive agent and exhibiting desired sol-gel transition temperatures and/or gel dissolution rates.

It is yet another objective of the present invention to provide gelling compositions, and methods of their use in preventing or reducing adhesions, which exhibit desired sol-gel transition temperatures and/or gel dissolution rates.

SUMMARY OF THE INVENTION

The present invention accomplishes these and other objectives by providing polymeric compositions that exhibit well defined sol-gel transition temperatures (or defined ranges of temperatures) and/or established dissolution rates. In one embodiment, the disclosed compositions generally comprise at least one constitutive polymer and at least one modifier polymer that may be used to modify or control the dissolution rate of gel once it has been formed. In another preferred embodiment, the compositions of the present invention comprise at least one constitutive polymer and at least one hydrophilic co-surfactant whereby the gelation temperature (or sol-gel transition temperature) of the composition may be controlled or modified. Of course, it will be appreciated that the compositions may comprise at least one constitutive polymer in combination with both at least one modifier polymer and at least one hydrophilic co-surfactant to provide preparations having both selected gelation temperatures and superior dissolution times. Yet other preferred embodiments of the invention will comprise the aforementioned preparations and at least one bioactive agent. In any event, the polyphase preparations of the present invention may be used to retard or prevent the formation of scar tissue or adhesions in a mammal, for the prolonged delivery of a bioactive agent or both.

Accordingly, in selected embodiments the present invention comprises methods for the reduction of adhesion or scar tissue formation comprising the administration of the disclosed preparations to a mammal in need thereof. Yet other selected embodiments comprise methods of delivering a bioactive agent to a mammal comprising administering the disclosed polyphase compositions incorporating a pharmaceutically effective amount of at least one bioactive agent to a mammal in need thereof. With respect to each of the aforementioned embodiments the compositions of the present invention will be administered as a relatively free flowing liquid that gels upon contact with the mammalian tissue to provide a viscoelastic semi-solid barrier or mask that may remain in place for an extended period.

In preferred embodiments of the instant invention the constitutive polymer will be a polyoxyalkylene copolymer. More particularly, in selected embodiments the constitutive polymer will be selected from the group consisting of polyoxyalkylene block copolymers, polyoxyalkylene polyethers and combinations thereof. In especially preferred embodiments of the invention, the constitutive polymer will comprise Poloxamer 407. The constitutive polymer or polymers may be present at any concentration that provides the desired gel viscosity and/or viscoelastic properties. Preferably, the constitutive polymers are present in a concentration which, when combined with the other components of the preparation, allows for the administration of the composition as a relatively free flowing liquid which gels upon contact with mammalian tissue.

Besides the constitutive polymer discussed above, selected embodiments of the invention will comprise at least one modifier polymer that may be used to modify the dissolution rate of the composition. Essentially, modifier polymers compatible with the present invention comprise any polymeric entity capable of slowing or retarding the dissolution rate of the constitutive polymer once it has gelled. That is, the modifier polymers of the present invention comprise any polymer that, when added to the constitutive polymer(s), provides for a slower dissolving or diffusing gel when compared with a gel formed from pure constitutive polymer(s) under equivalent conditions. Preferred modifier polymers typically have a relatively high average molecular weight on the order of tens or hundreds of thousands. While a large number of polymeric compounds are suitable for use as modifier polymers, particularly preferred compounds comprise cellulose ethers (carboxymethyl cellulose) and Carbopols (e.g. Carbopol 940-NF). The absolute incorporated concentration of the modifier polymers in the compositions of the present invention is not critical and may be adjusted to provide the desired dissolution rates and/or retention times.

In addition to the aforementioned elements, selected embodiments of the compositions disclosed herein may further comprise one or more hydrophilic co-surfactants which may be used to modify the gelation temperature (sol-gel transition temperature) of the resulting preparation. More particularly, selected hydrophilic co-surfactant(s) may be added to compositions comprising a constitutive copolymer(s) or compositions comprising constitutive copolymer(s) and modifier polymer(s) to alter or modify the gelation temperature of the resulting composition when compared to similar compositions not comprising the hydrophilic co-surfactant. In especially preferred embodiments the hydrophilic may be added at an effective concentration to lower the gelation temperature of the composition so as to provide for more rapid and complete gelation upon contact with the relatively high temperature mammalian tissue. While a number of compounds may be used as hydrophilic co-surfactants in accordance with the teachings herein, particularly preferred embodiments of the present invention incorporate fatty acid soaps such as sodium laureate, sodium caprate or sodium caprylate. Of course it will be appreciated that combinations of hydrophilic co-surfactants may be incorporated in the compositions of the present invention to provide the desired transition temperature or transition temperature range.

As previously alluded to the preparations of the present invention may further include one or more selected bioactive agents. More specifically, pharmaceutically effective amounts of both hydrophilic and lipophilic bioactive agents may be advantageously delivered using the preparations of the present invention. Thus, in accordance with the aforementioned embodiments, bioactive agents compatible with the present invention include, but are not limited to, antibiotics, antivirals mydriatics, antiglaucomas, anti-inflammatories, antihistaminics, antineoplastics, anesthetics, ophthalmic agents, enzymes, cardiovascular agents, polynucleotides, genetic material, viral vectors, immunoactive agents, imaging agents, immunosuppressive agents, peptides, proteins, physiological gases, gastrointestinal agents and combinations thereof. Particularly preferred compositions may comprise one or more humectants, bactericides, bacteriostatic agents, fibrinolytic agents or agents effective in preventing leukocyte migration into the area of surgical injury. Pharmaceutically effective amounts of the selected bioactive agents may be determined using techniques well known in the art. It will further be appreciated that the bioactive agents may be incorporated in the form of relatively insoluble solid particulates or associated with insoluble polymeric particulates.

It will be appreciated that, in accordance with the teachings herein, the preparations of the present invention, with or without an incorporated bioactive agent, may be administered to a patient using a route of administration selected from the group consisting of topical, subcutaneous, pulmonary, synovial, intramuscular, intraperitoneal, nasal, vaginal, rectal, aural, oral and ocular routes. The administered composition preferably gels upon contact with the relatively warm mammalian tissue and may act as a depot for the prolonged delivery of one or more incorporated bioactive agents. In other embodiments the gelled compositions may act as a barrier or film which prevents or retards the formation of adhesion or scar tissue. Since the present invention provides particularly effective methods for the prevention of post-surgical and other adhesion formation, administration of pharmaceutically effective amounts to the peritoneal, pelvic or pleural cavity is especially preferred. As such adhesions are often associated with injury to mammalian organs, those skilled in the art will appreciate that the compositions are particularly useful when applied to the selected area during or immediately following surgery.

Besides the components mentioned above, the compositions of the present invention may further comprise pharmaceutically acceptable stabilizers, preservatives and buffers, preferably in an amount sufficient to maintain the pH of the composition at about pH 7.4±0.2.

Other objects, features and advantages of the present invention will be apparent to those skilled in the art from a consideration of the following detailed description of preferred exemplary embodiments thereof taken in conjunction with the associated Figures which will first be described briefly.

DETAILED DESCRIPTION OF THE INVENTION

Figure 1:
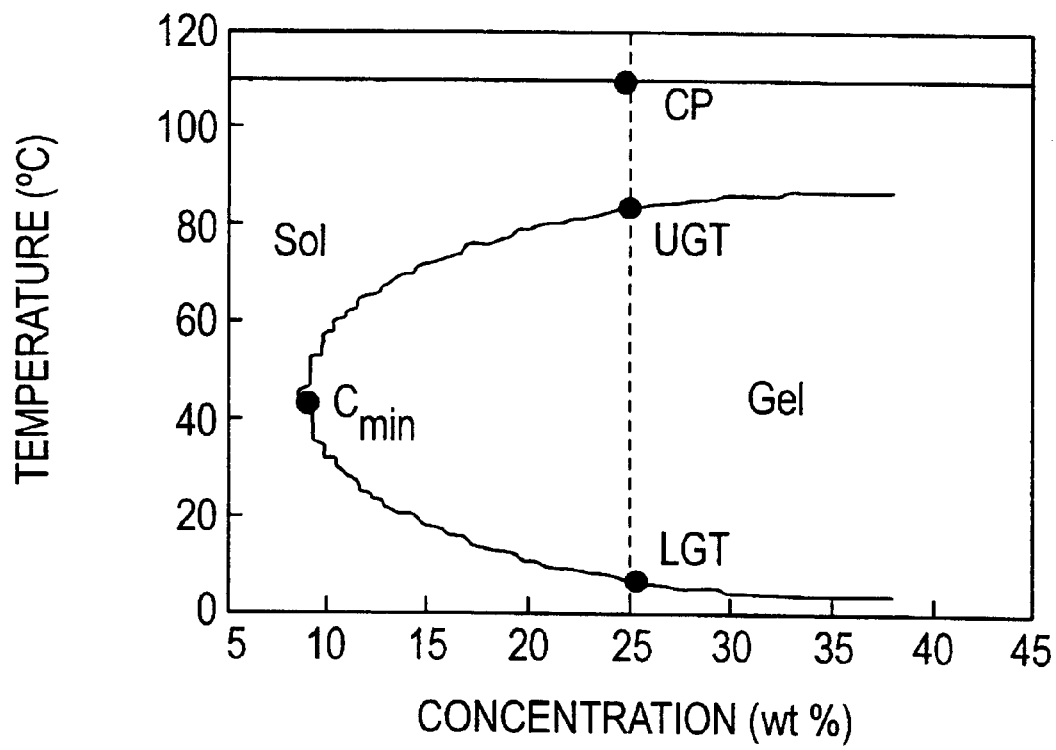
FIG. 1 is a graphical representation of an exemplary phase diagram for a prior art composition comprising a constitutive polymer.

Compositions and methods are disclosed herein for delivering bioactive agents and/or reducing post-surgical adhesion formation/reformation in mammals following injury to the organs or tissues, particularly those of the peritoneal, pelvic or pleural cavity. The compositions of the invention are also useful in reducing adhesion formation/reformation in other body spaces such as the subdural, extraocular, intraocular, otic, synovial, tendon sheath, or those body spaces created either surgically or accidentally. In selected embodiments of the invention, the concentration of the constitutive polymer in the disclosed compositions may be adjusted to take advantage of the gelation properties of certain polyoxyalkylene polymers. For instance, at certain concentrations aqueous solutions of said polymers form clear gels at mammalian body temperatures but are liquids at ambient temperatures or below. Of course, it is a major advantage of the present invention that selected hydrophilic co-surfactants may also be used to modify the gelation temperature of the disclosed compositions. This advantageously allows the selected compositions of the present invention to be administered as a relatively free flowing liquid which gels or thickens at the body temperature of the mammalian subject. However, it should be appreciated that compositions may be formed in accordance with the teachings herein that do not gel or thicken following application to the selected area or tissue.

Preferably, the osmolality and pH of the compositions are adjusted to match the pH and osmotic pressure of mammalian bodily fluids, i.e. approximately pH 7.4. Subsequent to deposition of the compositions of the invention in the peritoneal, pelvic, or pleural cavity of a mammal, or other body spaces the constitutive polymer (i.e., a polyoxyalkylene block copolymer) is eventually excreted in a non-metabolized form, mainly through the kidney.

The present compositions may also be used as a distending medium during diagnostic or operative endoscopic procedures, such as, for example, for intrauterine procedures. In addition to the anti-adhesive properties, since certain aqueous concentrations of the preferred polyoxyalkylene block copolymers form a clear gel, their use is well suited for visualization of interior cavities.

In a further advantage, the disclosed formulations provide a barrier between tissues for hours or days. Because they are applied as liquids, they are easier to use, particularly for laparoscopic surgical procedures. That is, the compositions of the instant invention may be administered though a relatively small incision using a cannula or catheter assembly.

Those skilled in the art will appreciate that the disclosed compositions of the present invention are preferably aqueous based preparations. Thus, the compositions typically comprise water in an amount of from about 60% to about 90%, by weight, preferably, about 70% to about 85%, by weight, and most preferably, about 75% to about 82% by weight, based upon the total weight of the composition.

As used herein, the terms "peritoneal" and "abdominal" cavity are used as synonyms, as are the terms "pleural" and "thoracic" cavity.

As used herein, the term "polyalkylene block polymers" include those polymers which form clear gels at mammalian body temperatures but are liquids at ambient temperatures or below.

As used herein, the term "gel" is defined as a solid or semisolid colloid containing a certain quantity of water. The colloidal solution with water is often called a "hydrosol".

A. Constitutive Polymers:

As set forth above, the present invention comprises at least one constitutive polymer dispersed in a aqueous medium. In preferred embodiments of the instant invention the constitutive polymer will be a polyoxyalkylene polymer. More particularly, in selected embodiments the constitutive polymer will be selected from the group consisting of polyoxyalkylene block copolymers, polyoxyalkylene polyethers and combinations thereof. In especially preferred embodiments of the invention, the constitutive polymer will comprise poloxamer 407. The constitutive polymer or polymers may be present at any concentration that provides the desired gel viscosity and/or viscoelastic properties. Preferably, the constitutive polymers are present in a concentration which, when combined with the other components of the preparation, allows for the administration of the composition as a relatively free flowing liquid which gels upon contact with mammalian tissue.

Thus, according to a preferred embodiment, the compositions comprise one or more polyoxyalkylene block copolymers of the formula

(I)

wherein A is a polyoxyalkylene moiety;

x is at least 2;

Y is derived from water or an organic compound containing x reactive hydrogen atoms;

E is a polyoxyethylene moiety;

n has a value such that the average molecular weight of A is at least about 500; and the total average molecular weight of the copolymer is at least about 5000.

Preferably, the polyoxyalkylene moiety A has an oxygen/carbon atom ratio of less than 0.5. According to one embodiment of the invention, A is derived from an alkylene oxide selected from the group consisting of butylene oxide, propylene oxide or a mixture thereof. Preferably, A is a polyoxypropylene moiety, and preferably has an average molecular weight of from about 3,000 to about 4,000 g mol$^{-1}$.

The polyoxyethylene moiety E preferably constitutes from about 60 to about 85% by weight of the copolymer, more preferably at least about 70%.

In one embodiment, Y is derived from a water soluble organic compound having 1 to about 6 carbon atoms. In another embodiment, Y is derived from an organic compound selected from the group consisting of propylene glycol, glycerin, pentaerythritol trimethylolpropane, ethylenediamine and mixtures thereof.

According to one embodiment, the copolymer has the formula:

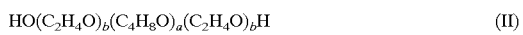

$$HO(C_2H_4O)_b(C_4H_8O)_a(C_2H_4O)_bH \qquad (II)$$

wherein a and b are integers such that $(C_4H_8O)_a$ has a molecular weight of at least about 500.

Useful polyoxyalkylene block copolymers which will form gels in aqueous solutions can be prepared using a hydrophobe base (such as A in Formulas (I) and (II)) derived from propylene oxide, butylene oxide or mixtures thereof. These block copolymers and representative methods of preparation are further generally described in U.S. Pat. Nos. 2,677,700; 2,674,619; and U.S. Pat. No. 2,979,528, incorporated herein by reference.

Generally, the polyoxybutylene-based block copolymers useful in the compositions of the invention are prepared by first condensing 1,2 butylene oxide with a water soluble organic compound initiator containing 1 to about 6 carbon atoms such as 1,4 butylene glycol or propylene glycol and at least 2 reactive hydrogen atoms to prepare a polyoxyalkylene polymer hydrophobe of at least about 500, preferably at least about 1000, most preferably at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are herein incorporated by reference.

In a further preferred embodiment, the compositions comprise polyoxyethylene-polyoxypropylene block copolymers of the formula (III):

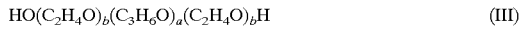

$$HO(C_2H_4O)_b(C_3H_6O)_a(C_2H_4O)_bH \qquad (III)$$

wherein a is an integer such that the hydrophobe base represented by $(C_3H_6O)_a$ has a molecular weight of at least about 900, preferably at least about 2500, most preferably at least about 4000 average molecular weight, as determined by hydroxyl number. In a particularly preferred embodiment, the compositions comprise a polyxyethylene-polyoxyproplyene block copolymer of formula (III), having a polyoxyproplyene hydrophobe base average molecular weight of about 4000, a total average molecular weight of about 12,000 and containing oxyethylene groups in the amount of about 70% by weight of the total weight of the copolymer. This copolymer is sold under the trademark PLURONIC® F-127 (also known as poloxamer 407)(BASF Corp, Parsippany, N.J.).

More specifically, poloxamer 407 is a tri-block copolymer containing two polyoxyethylene blocks flanking a central polyoxypropylene block. The USP material has an average molecular formula of $(EO)_{101}$-$(PO)_{56}$-$(EO)_{101}$, and average molecular weight of ca. 12,000 g mol$^{-1}$. When placed in an aqueous solution in accordance with the present invention, poloxamer 407 self-assembles so as to remove contact between the polyoxypropylene groups and water (i.e. self-assembly is driven by the hydrophobic effect). The self-assembled units are termed micelles. The structure of the micelles and the interactions between them is strongly dependent on temperature. Interestingly, a large increase in solution viscosity (i.e. gel-phase formation) is noted with increasing temperature. Gel phase formation occurs as a result of organization of the micelles into a three-dimensional cubic array.

In another embodiment, the copolymer has the formula:

$$(R)_2N-(CH_2)_2-N(R)_2 \qquad (IV)$$

wherein R is $H(OC_2H_4)_b(OC_3H_6)_a-$; and a and b are integers such that the hydrophobe base represented by $(C_3H_6O)_a$ has a sum average molecular weight of at least about 2000, about 3 to about 5%. The hydrophobe base is prepared by adding propylene oxide for reaction at the site of the four reactive hydrogen atoms on the amine groups of ethylenediamine. An ethylene oxide residue is used to cap the hydrophobe base.

In all permutations of copolymers of formula (I), it is preferred that the polyoxyethylene chain constitute from about 60 to about 85% by weight of the colpolymer, preferably at least about 70%. It is further preferred that the copolymer have a total average molecular weight of at least about 5000, preferably from about 9,000 to about 15,000 as specified in the USP).

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C., with slow stirring until a clear homogeneous solution is obtained. Upon cooling, a clear gel is formed. Block copolymer gels containing polyoxybutylene hydrophobes must be prepared by the above hot process, since these will not liquefy at low temperatures.

The organic compound initiator which is utilized in the preparation of the polyoxyalkylene block copolymers generally is water or an organic compound, and can contain a plurality of reactive hydrogen atoms. Preferably, Y in formulas (I) and (II) above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylenediamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste or a solid granular material depending upon the molecular weight of the polymer.

In addition to those polyoxyalkylene polymers described above, the present compositions may comprise other polyoxyalkylene polymers which form gels at low concentrations in water. Examples of such polymers are described in U.S. Pat. No. 4,810,503, incorporated herein by reference. These polymers are prepared by capping conventional polyoxyalkylene polyether polyols with an alphaolefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant which generally do not exceed 10% by weight total.

Conventional copolymer polyether polyols are prepared by preparing block or heteric intermediate polymers of ethylene oxide and at least one lower alkylene oxide having 3 to 4 carbon atoms as intermediates. These are then capped with the alpha-olefin epoxide. Ethylene oxide homopolymers capped with the alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 1500 C, preferably, from 80° C. to 130°, under an inert gas pressure, preferably, from about 30 psig to 90 psig.

A block copolymer intermediate is prepared by reacting either the ethylene oxide or the alkylene oxide having 3 to 4 carbon atoms with the active hydrogen-containing compound followed by reaction with the other alkylene oxide.

The ethylene oxide and the alkylene oxides having from 3 to 4 carbon atoms are used in the intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with the active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediates are those oxides, and commercially available mixtures thereof, generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers.

Further description regarding the preparation of heteric and block copolymers of alkylene oxides and ethylene oxide homopolymers is described in the art (U.S. Pat. Nos. 3,829,506, 3,535,307; 3,036,118; 2,979,528; 2,677,700; and 2,674,619, incorporated herein by reference.)

Whatever constitutive polymer is selected the absolute concentration present in the compositions of the present invention is determined by the gelation characteristics desired. One major advantage of the present invention is that the desired gelation temperatures and viscosity of the resulting gels may be adjusted through the addition of modifier polymers and hydrophilic co-surfactants. This allows the use of lower concentrations of constitutive polymer without markedly reducing the ultimate gel characteristics of the composition.

However, for the purposes of the present invention, exemplary concentrations of constitutive polymer may range from approximately 2% w/w to 50% w/w and more preferably from 4% to 30% w/w and even more preferably from 16% to 28% w/w.

B. Modifier Polymers:

As set forth above any biocompatible polymeric entity that modifies the dissolution time of the gel resulting from the administration of the compositions of the present invention may be used in accordance with the teachings herein. In general terms, preferred modifier polymers to alter the dissolution time should preferably have the following characteristics: (a) high molecular weight; (b) effective swelling in water but poor dissolution: (c) compatibility with the constitutive polymer and, in particular, poloxamers; and (d) stability to extremes in heat and pH. Those skilled in the art will appreciate that the phrase "alter the dissolution time" is held to mean the alteration of the gel dissolution time in vitro or in vivo with respect to a gel comprising constitutive polymer without the modifier polymer under similar conditions. It will further be appreciated that the alteration of dissolution times or release rates of the constitutive polymer from the gel matrix may be used to optimize formulations for antiadhesion applications as well as for other applications including controlled drug delivery.

Without wishing to be bound by any one particular theory, it is believed that release (and subsequent gel dissolution) is a function of several physicochemical characteristics within the gel, and can be modified by the addition of high molecular weight polymers such as sodium carboxymethyl cellulose, polyacrylates (i.e. Carbopols) or other polyester based polymers. It appears that the dissolution rate is modified by the formation of a strong polymeric matrix (i.e. the modifier polymeric matrix) that controls the release of the constitutive polymer via diffusion through the formed modifier polymer interstices. One possible reason for this effect may be that the constitutive polymer has to diffuse around the long linear molecules of the incorporated modifier polymer. In general, this effect appears to be most pronounced when the selected modifier polymer(s) have a molecular weight greater than or equal to approximately 500,000 although modifier polymers of much lower molecular weight (i.e. on the order of 50,000). In particularly preferred embodiments the selected modifier polymers will combine a relatively high molecular weight with a biodegradable moiety in their structure to speed excretion. High molecular weight polylactic-glycolide copolymers which are broken down by hydrolytic decomposition are one example of such a polymer. It should be emphasized that these modifier polymers may also be used to slow the dissolution (and hence prolong delivery time) of any incorporated bioactive agent.

While any polymeric entity possessing the appropriate characteristics may be incorporated in the compositions of the present invention, exemplary polymers compatible with the teachings herein include, but are not limited to: poly(acrylic acid), poly(stirene sulfonate), carboxymethylcellulose, poly(vinyl alcohol), poly(ethylene oxide), poly(vinylpyrrolidone), shellac, cellulose acetate phthalate, cellulose acetate succinate, polyvinyl acetate phthalate, hydroxypropylmethylcellulose acetate, poly(methacrylic acid-co-methylmethacrylate), poly(methyl acrylate), poly(methyl methacrylate), poly(glutamic acid), poly(lactic acid), poly(lactic-glycolide), poly(glycolic acid), poly(ε-caprolactone), poly(β-hydroxybutyric acid), poly(β-hydroxyvaleric acid), polydioxanone, poly(ethylene terephthalate), poly (malic acid), poly(tartronic acid), poly (ortho esters), polyanhydrides, polycyanoacrylate, poly(phosphoesters), polyphosphazenes, poly(lysine), polysaccharides, chitosan, polyelectrolytes, gelatin, gum arabic, poly(amino acids), agar, furcelleran, alginate, carageenan, starch, pectin, celluloses, exudate gums, tragacanth, karaya, ghatti seed gums, guar gum, locust bean gum, xanthan, pullulan, scleroglucan, curdlan, dextran, gellan, chitin, chondroitin sulfate, water soluble collagen, dermantan sulfate, heparin, keratan sulfate, hyaluronic acid and combinations thereof It will further be appreciated that any pharmaceutically acceptable salt of the foregoing compounds may be used in the disclosed compositions with compromising the effectiveness thereof.

As will be seen in the Examples below the modifier polymers of the present invention may be used in suprisingly low concentrations to provide extended dissolution times or release times. In this regard, the selected modifier polymers are preferably incorporated in a range between about 0.05% and about 25% by weight and more preferably in a range of from approximately 0.5% to approximately 5% by weight. Of course the absolute amount of modifier polymer included in the composition will depend on factors such as the constitutive polymer selected, the molecular weight of the modifier polymer and the physiochemical properties of the various composition components. These determinations are well within the purview of the skilled artisan and may easily be determined without undue experimentation.

C. Hydrophilic Co-Surfactants:

Yet another aspect of the present invention comprises the addition of a hydrophilic co-surfactant to the disclosed compositions (i.e. constitutive polymer preparations and constitutive polymer+modifier polymer preparations) to alter the physiochemical properties thereof. That is, the incorporation of a hydrophilic co-surfactant in accordance with the teachings herein may provide several advantages over prior art formulations. These advantages are most easily understood in conjunction with a graphical representation of a polyphase system of the instant invention and examples set forth below.

Accordingly, turning to FIG. 1 a phase diagram for a constitutive polymer solution (poloxamer 407) is shown. The lower gelation temperature (LGT) refers to the temperature at which the poloxamer micelles (sol phase) self-assemble into the cubic array (i.e. the gel phase). At temperatures above the upper gelation temperature (UGT) the micelles change their shape from spheres to prolates, thereby negating their ability to assemble in a cubic packing. This leads to the reformation of the low viscosity sol phase. Above another critical temperature, termed the cloud point (CP), the micelles separate into their own coacervate phase in excess water. The solution clouds due to mixing of the two insoluble phases.

The lower gelation temperature (LGT) of the constitutive polymer solutions in water is largely dependent upon the total constitutive polymer concentration, such that increases in concentration lead to decreases in the LGT. Fractionation of the constitutive polymer (fractionated using organic phase separation or other means known in the art, such as described, for example, in *Textbook of Polymer Science,* F. Billmeyer, Wiley-Interscience, pp. 45–56 (1971)) and the addition of high viscosity carboxymethylcellulose (CMC) does little to alter the LGT. FloGel 28 (28% w/w poloxamer 407) has an LGT of 13° C., and is currently applied surgically at a temperature of 0° C. Therefore, application of the product will have to be done in a timely fashion to avoid gelation in the application catheter. Additionally, it has been hypothesized that increases in the LGT to a temperature close to or above room temperature may be advantageous.

As previously discussed, the equilibrium phase behavior of solutions comprising a constitutive polymer can be dramatically altered by the addition of hydrophilic co-surfactants. The changes in phase behavior are typically manifested by significant increases in the lower gelation temperature and cloud point temperature. While any hydrophilic co-surfactant may be used to modify the equilibrium phase behavior of the disclosed compositions in accordance with the teachings herein, hydrophilic co-surfactants comprising fatty acid soaps are particularly compatible with the present invention. In this regard long chain, saturated soaps appear to be particularly efficient at altering the phase behavior to provide the desired composition characteristics. Significantly, the Theological properties of the gelled compositions of the present invention are unaltered by the presence of the fatty acid soaps, indicating that, as long as the critical packing volume of the cubic phase is exceeded, the rheology will remain virtually unchanged. Thus, in accordance with the instant invention, the addition of hydrophilic co-surfactants to the disclosed polyphase systems provides an efficient method for modifying the gelation temperature and cloud point temperature. These changes in phase behavior are particularly advantageous for a drug delivery vehicle or antiadhesion product as they allow for storage and application at temperatures near room temperature. Moreover, these characteristics reduce the potential for significant syneresis during terminal sterilization.

Accordingly, preferred embodiments of the present invention may comprise effective amounts of at least one hydrophilic co-surfactant. In particularly preferred embodiments the incorporated hydrophilic co-surfactant will comprise a fatty acid soap. Those skilled in the art will appreciate that fatty acid soaps are GRAS (generally regarded as safe) materials, present naturally in the human body, and included in many pharmaceutical products including large volume parenterals (e.g. Fluosol®). Their toxicological profile is well understood and, at the concentrations compatible with the present invention, they pose no toxicological risk. While several compounds comprising fatty acids are useful in the present invention, especially compatible fatty acid soaps comprise sodium oleate, sodium laurate, sodium caprate, sodium caprylate and combinations thereof.

In any event, as illustrated by the Examples below, the hydrophilic co-surfactants of the present invention may be incorporated in relatively low concentrations to provide the desired gelation properties. It will be appreciated that the selected hydrophilic co-surfactant or surfactants may comprise any concentration that provides for the preferred gelation temperatures. However, exemplary concentrations of hydrophilic co-surfactants compatible with the instant invention are typically in a range between about 0.05% and about 25% by weight and more preferably in a range of from approximately 0.5% to approximately 5% by weight.

D. Bioactive Agents:

In addition to the antiadhesion characteristics of the compositions of the present invention the preparations also provide for the efficient delivery of bioactive agents. Along with the prolonged deposition time supplied by the disclosed compositions, they may increase the solubilization and bioavailability of incorporated pharmaceutical compounds. More particularly, the micelle core of the gelled compositions of the present invention may serve as a reservoir for solubilizing nonpolar solutes such as hydrophobic drugs. Interestingly the micelles may also self-assemble to form stiff gels above a critical temperature. As previously discussed, gel formation appears to occur when the micelles behave as hard spheres in a close-packed simple cubic array. This thermal gelation property provides interesting formulation alternatives for pharmaceutical applications, whereby the poloxamer micelles are applied in the fluid sol state and allowed to gel in place on tissue surfaces. Thus, in addition to their ability to act as a barrier to prevent surgical adhesions, poloxamer gels may also be an ideal drug delivery vehicle, owing to their low toxicity and ability to impede drug diffusion.

Accordingly, the compositions disclosed herein may further optionally comprise one or more pharmaceutically acceptable adjuvants such as a humectant, a bactericide, a bacteriostatic agent, an antihistamine, or a decongestant, an agent to prevent leucocyte migration into the area of surgical injury, or a fibrinolytic agent. Useful humectants include, but are not limited to, glycerin, propylene glycol and sorbitol. Useful bactericides include, by way of example, antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fluoroalanine/pentizidone; nitrofurazones, and the like. Antihistamines and decongestants such as pyrilamine, chlorpheniramine, tetrahydrozoline, antazoline, and the like, can also be used in admixtures as well as anti-inflammatories such as cortisone, hydrocortisone, beta-methasone, dexamethasone, fluocortolone, prednisolone, triamcinolone, indomethacin, sulindac, its salts and its corresponding sulfide, and the like. Both steroidal and nonsteroidal compounds are particularly compatible with the compositions and methods of the present invention. With regard to the latter, ketoprofen, indomethacin and tolmetin sodium are particularly preferred. Nitric oxide donors such as nononates and nitrosylated compounds may also be incorporated. Useful leucocyte migration preventing agents which can be used in admixtures include but are not limited to silver sulfadiazine, acetylsalicylic acid, indomethacin and Nafazatrom. Useful fibrinolytic agents include urokinase, streptokinase, tissue plasminogen activator (TPA) and acylated plasmin.

In a more general sense, compatible bioactive agents comprise both hydrophilic and lipophilic compounds including antibiotics, antivirals, mydriatics, antiglaucomas, anti-inflammatories, antihistaminics, antineoplastics, anesthetics, ophthalmic agents including antiglaucomics, enzymes, cardiovascular agents, polynucleotides, genetic material, viral vectors, immunoactive agents, imaging agents, immunosuppressive agents, peptides, proteins, physiological gases, gastrointestinal agents and combinations thereof.

Because the preparations of the present invention are uniquely suited for various administrative techniques such as ocular, oral, pulmonary, rectal, synovial, subcutaneous, intramuscular, intraperitoneal, nasal, vaginal, or aural administration of medicaments or diagnostic compounds, they are compatible for use with a wide variety of bioactive agents. For example, ophthalmic applications involving topical administration of the disclosed preparations are particularly preferred. Accordingly, the foregoing list of compounds is exemplary only and not intended to be limiting. It will also be appreciated by those skilled in the art that the proper amount of bioactive agent and the timing of the dosages may be determined for the formulations in accordance with already-existing information and without undue experimentation.

Preferably, the compositions are applied to surgically injured tissue as an aqueous solution which upon contact with living mammalian tissue forms a firm, adherent gel. Where the composition is a viscous liquid or paste, these compositions can be applied without dilution to areas of surgical injury in the abdominal or thoracic cavities. The formulations adhere to the site of tissue injury and reduce or prevent the formation of postsurgical adhesions during the healing process.

In addition to the aforementioned applications, the preparations of the invention may also be used to deliver therapeutic and diagnostic agents to the gastrointestinal tract by, for example, the oral or direct routes of administration. A contemplated example would be the delivery of antibiotics to the lining of the gastrointestinal tract in the treatment of *Heliobacter pylori* infections. *H. pylori* has been implicated in the cause of gastric ulcers and stomach cancer. Antibiotics effective in the treatment of *H. pylori* infections could be administered in the form of a free flowing liquid that gels and adheres to the sites of infection.

It will be appreciated that the compositions of the present invention may further contain preservatives, cosolvents, suspending agents, viscosity enhancing agents, ionic-strength and osmolality adjustors and other excipients in addition to buffering agents. Suitable water soluble preservatives which may be employed are sodium bisulfite, sodium thiosulfate, ascorbate, benzalkonium chloride, chlorobutanol, thimerosal, phenylmercuric borate, parabens, benzylalcohol phenylethanol and others. These agents may be present, generally, in amounts of about 0.001% to about 5% by weight and, preferably, in the amount of about 0.01 to about 2% by weight.

Suitable buffering agents or salts useful in maintaining pH include alkali or alkaline earth metal carbonates, chlorides, sulfates, phosphates, bicarbonates, citrates, borates, acetates and succinates such as sodium phosphate, citrate, borate, acetate, bicarbonate, carbonate and tromethamine (TRIS). Preferably, these agents are present in amounts sufficient to maintain the pH of the system at 7.4±0.2 and preferably, 7.4. As such, the buffering agent can be as much as 5% by weight.

It will also be appreciated by those skilled in the art that the preparations of the present invention may be sterilized, for example, by heat, irradiation, ultrafiltration or combinations of any of these or equivalent techniques. Specifically, the preparations of the invention may be sterilized, for example, by autoclaving at 121° C. for 15 minutes or by filtration through a 0.22 mm filter.

The high bioavailability bioactive preparations of the present invention may advantageously be supplied to the physician in a sterile prepackaged form. More particularly, the formulations may be supplied as stable, preformed preparations, ready for administration or as separate, ready to mix components. When supplied as components the final preparation of the polyphase material could easily be performed in the pharmacy just prior to administration.

The following examples illustrate the various aspects of the invention but are not intended to limit its scope. Where not otherwise specified throughout this specification and claims, temperatures are given in degrees centigrade, and parts, percentages, and proportions are by weight.

EXAMPLE 1

Synthesis of Compositions Comprising Modifier Polymers

Compositions comprising a constitutive polymer (poloxamer 407) and a modifier polymer (sodium carboxymethylcellulose) were prepared by dissolving the poloxamer in distilled water (4° C.) to give a concentration of 28% by weight in accordance with the cold process described above for forming aqueous solutions.

Formulation 1: FloGel 28B (Control)

| Ingredients | Source | Lot | % w/w grams |
|---|---|---|---|
| Poloxamer 407, NF, Prill 280.00 | BASF | WPDP-586B | 28.0000 |
| Tromethamine (TRIS), USP 1.09 | Spectrum | ID 289 | 0.1091 |
| Maleic Acid 1.5 | Spectrum | IK 051 | 0.1045 |
| Sodium Hydroxide Pellets, USP 0.42 | Spectrum | IG 043 | 0.0420 |
| Sterile Water for Irrigation, USP 717.44 1000 | Baxter | G876094 | 71.7444 Total |

Formulation 2: FloGel 25B/0.5

| Ingredients | Source | Lot | % w/w grams |
|---|---|---|---|
| Poloxamer 407, NF, Prill 250.00 | BASF | WPDP-586B | 25.0000 |
| Sodium Carboxymethylcellulose 5.00 | Spectrum | JA 156 | 0.5000 |
| Tromethamine (TRIS), USP 1.09 | Spectrum | ID 289 | 0.1091 |
| Maleic Acid 1.05 | Spectrum | IK 051 | 0.1045 |
| Sodium Hydroxide Pellets, USP 0.42 | Spectrum | IG 043 | 0.0420 |
| Sterile Water for Irrigation, USP 742.44 1000 | Baxter | G876094 | 74.2444 Total |

Formulation 3: FloGel 20F/0.8

| Ingredients | Source | Lot | % w/w grams |
|---|---|---|---|
| Poloxamer 407, Fractioned 200.00 | MDV | 1145-107 | 20.0000 |
| Sodium Carboxymethylcellulose 8.00 | Spectrum | JA 156 | 0.8000 |
| Tromethamine (TRIS), USP 1.09 | Spectrum | ID 289 | 0.1091 |
| Maleic Acid 1.05 | Spectrum | IK 051 | 0.1045 |
| Sodium Hydroxide Pellets, USP 0.42 | Spectrum | IG 043 | 0.0420 |
| Sterile Water for Irrigation, USP 789.44[001b] 1000 | Baxter | G876094 | 72.7444 Total |

Formulation 4: FloGel 16B/1.5

| Ingredients | Source | Lot | % w/w grams |
|---|---|---|---|
| Poloxamer 407, NF, Prill 160.00 | BASF | WPDP-586B | 16.0000 |
| Sodium Carboxymethylcellulose 15.00 | Spectrum | JA 156 | 1.5000 |
| Tromethamine (TRIS), USP 1.09 | Spectrum | ID 289 | 0.1091 |
| Maleic Acid 1.05 | Spectrum | IK 051 | 0.1045 |
| Sodium Hydroxide Pellets, USP 0.42 | Spectrum | IG 043 | 0.0420 |
| Sterile Water for Irrigation, USP 822.44 1000 | Baxter | G876094 | 82.2444 Total |

EXAMPLE 2

Anti-adhesion Characteristics of Compositions Comprising Modifier Polymers

The following test procedure was utilized to determine the effect of the formulations of Example 1 on surgically injured rats. Female Sprague-Dawley rats having a 300–400 gram body weight were anesthetized with pentobarbital sodium (30 milligrams per kilogram of body weight) by application intrapertoneally through the left lumbar region of the ventral abdominal wall. Surgical defects (2) were created in directly opposed proximity by excising the peritoneal membrane and thereby exposing sidewall muscle tissue (2×1 cm). The outer membrane of the cecum was removed by surgical peeling, thus exposing blood vessel loops (2×1 cm). Both exposed defects were abraded to cause petechial bleeding, and then exposed to direct radiant heat source for 15 minutes to accelerate desiccation. One ml of the compositions of Example 1 (application temperature of 0° C.) was applied to one injured site. The other injured site was left untreated.

Results of this experiment indicate that a formulation containing only poloxamer 407 (Formulation 1) reduced adhesions by approximately 50%, while formulations containing poloxamer 407 and carboxymethylcellulose (Formulations 2–4) reduced adhesions by 70 to 99%. The increased efficacy of formulations containing both polymers may be due to a reduced rate of erosion in vivo analogous to that observed in vitro. All of the formulations exhibited maximal efficacy when applied to the injured tissue at approximately 0° C.

EXAMPLE 3

Dissolution Rates of Compositions Comprising Modifier Polymers

The following example is directed to the determination of dissolution rates for various formulations prepared in accordance with the teachings herein. Several of the formulations incorporate at least one modifier polymer.

Materials:

Chemicals utilized in the study and their sources are listed below, All chemicals were used without further purification.

Sodium phosphate dibasic, $Na_2HPO_4 \cdot 7H_2O$ (Sigma Chemical Co. St. Louis, Mo.)

Maleic acid sodium salt (Sigma Chemical Co., St. Louis, Mo.)

1 N hydrochloric acid solution (Fisher Scientific, Fair Lawn, N.J.)

Potassium nitrate (Fisher Scientific. Fair Lawn. N.J.)

0.1 N potassium hydroxide solution (Fisher Scientific, Fair Lawn, N.J.)

Methylene Chloride stabilized with amylene (Fisher Scientific. Fair Lawn, N.J.)

Picric Acid with 35% water (Aldrich Chemical Co., St. Louis. Mo.)

Tris(hydroxymethyl)-aminomethane (EM Science, Wakefield, R.I.)

Poloxamer 407 (BASF. Mount Olive, N.J.)

Fractionated Poloxamer 407 (APC Lot #9630201)

Carbopol 940 NF (BF-Goodrich. Cleveland, Ohio)

Hydroxypropylmethylcellulose K100M, HPMC-K100M, (Dow Chemical Company, Midland, Mich.)

Carboxymethylcellulose high viscosity, CMC (Spectrum Chemical Co., Gardena, Calif.)

Carboxymethylcellulose medium viscosity CMC-MV (Penta Manufacturing Co., Livingston, N.J.)

Preparation.

Polymer solutions were prepared by first dispersing the modifier polymer (i.e., CMC, hydropropylmethylcellulose (HPMC) or Carbopol) in the Tris/maleate buffer solution (0.1515 g of tris(hydroxymethyl)-aminomethane and 0.1726 g of sodium maleate were dissolved and brought up to 100 g with DI water) until fully hydrated. Poloxamer 407 (the constitutive polymer) was then added to the sample in an ice bath (T=3–5° C.), and mixed until the poloxamer dissolved. The sample was kept under refrigeration until usage.

In-vitro Dissolution Rate of Poloxamer Gels.

The in-vitro dissolution rates of poloxamer-based gels were determined using a modified USP dissolution apparatus (Hanson Research model SR6,) equipped with enhancer cells. Each of the dissolution vessels were filled with 25 mL of 0.1 M phosphate buffer (pH 7.4) (26.78 g of sodium phosphate dibasic ($Na_2HPO_4 \cdot 7H_2O$) was brought to a volume of 1 L with DI water) and left to equilibrate for about 20 minutes to 36.8° C. Membranes (1.2 μm cellulose ester membranes, 25 mm diameter, type RAWP) were presoaked in phosphate buffer and placed on the cell.

Approximately 0.6 mL of sample in the fluid sol phase was then loaded into each of the enhancer cells. The cells were subsequently closed and the fluid sol phase allowed to gel at room temperature prior to introduction into the dissolution vessels. The dissolution paddles were rotated at a speed of 100 rpm (approximating the hydrodynamic stress found in the peritoneal cavity) and were adjusted to remain at approximately 1 cm from the top of the cells throughout all experiments. The in-vitro release of poloxamer from the gels was monitored over a period of 4 hr, with 1 mL samples collected every 0.5 hr. The vessel was replaced with fresh buffer each time a sample aliquot was removed. Each sample was run in triplicate. The average standard error of the measurements was of 0.013.

Quantitation of Poloxamer.

The determination of poloxamer concentration in the aqueous phase was carried out using the potassium picrate spectrophotometric method. This method is based on the extraction of picrate ion from water into an organic solvent in association with potassium ion complexes of polyoxyethylene chains.

The procedure consists of mixing 250 μL of potassium picrate solution (0.23 g of picric acid (wet-based) dissolved in 10 mL of potassium hydroxide solution and brought to a volume of 50 mL with DI water) with 1 mL of 2.5 M potassium nitrate solution (50.55 g of potassium nitrate was brought up to a volume of 200 mL with DI water; the pH was then adjusted to 12 with 0.1 N KOH) and 0.1 mL of the sample containing the poloxamer solution in a 16×250 mm test tube. The mixture is then vortexed and extracted with 3 mL of $CH_2Cl_2$. The absorbance of the organic phase was measured at 378 nm vs. a reagent blank, with the concentration determined from a calibration curve (Table 1) prepared by adding aliquots of surfactant standard solution (1024 ug/mL). A Beckman UV/Vis spectrophotometer model DU-65 was used to measure poloxamer concentration. The pH was adjusted to 7.4 with 1N HCl using a Sentron pH meter.

TABLE I

| Poloxamer 407 Standard Solutions | | |
|---|---|---|
| Std ID | Poloxamer 407 (μg) | Absorbance (378 nm) |
| 1 | 64 | 0.245 |
| 2 | 128 | 0.497 |
| 3 | 256 | 0.982 |

Release Rates of Test Formulations:

The results obtained for various poloxamer-based formulations, including those comprising modifier polymers are detailed in Table II. The nomenclature of the various compositions is detailed below. FloGel 25 refers to a 25% w/w formulation of poloxamer 407 in the Tris/maleate buffer system. Should the letter F follow the number, the poloxamer 407 has been fractionated to remove low molecular weight impurities. For the purposes of this example, poloxamer 407 is the constitutive polymer. Should the formulation contain a modifier polymer, it follows after a slash. Thus, FloGel 20 F/0.5 C, contains 20% w/w fractionated poloxamer 407 and 0.5% w/w high viscosity grade CMC. The acronyms for the modifier polymers are denoted in Table II immediately below.

TABLE II

| In-Vitro Release Profiles of FloGels: | | | | |
|---|---|---|---|---|
| Sample | k ($hr^{-n}$) | n | b | MDT (hr) |
| Flogel 25 | 0.15 | 0.66 | 0.011 | 7 |
| Flogel 28 | 0.15 | 0.66 | 0.0026 | 7 |
| Flogel 28[a] | 0.97 | 1.0 | 0.009 | 1 |
| Flogel 28F | 0.22 | 0.5 | 0.099 | 7 |
| Flogel 25/0.5 C[a] | 0.78 | 0.8 | −0.041 | 1 |
| Flogel 25/0.5CMV | 0.22 | 0.5 | −0.040 | 7 |
| Flogel 25/1CMV | 0.23 | 0.5 | −0.032 | 6 |
| Flogel 25/0.5 HPMC | 0.17 | 0.5 | −0.023 | 11 |
| Flogel 25/0.5C | 0.14 | 0.5 | −0.0064 | 17 |
| FIogel 25/0.5 940 | 0.12 | 0.5 | −0.028 | 22 |
| Flogel 20F/0.5C | 0.10 | 0.5 | 0.001 | 33 |
| Flogel 20F/0.8C | 0.074 | 0.5 | 0.0053 | 60 |

TABLE II-continued

In-Vitro Release Profiles of FloGels:

| Sample | k (hr$^{-n}$) | n | b | MDT (hr) |
|---|---|---|---|---|
| Flogel 16/1.5C | 0.044 | 0.6 | 0.018 | 67 |
| Flogel 14F/1C | 0.037 | 0.6 | 0.019 | 90 | a No membrane used in dissolution study
F Fractionated Poloxamer 407
940 Carbopol 940-NF
C High Viscosity CMC
CMV Medium Viscosity CMC
HPMC Hydroxypropylmethylcellulose Discussion:

The data reported in Table II are fits to the Korsmeyer-Peppas equation V viz.

$$\frac{Q}{Q_\alpha} = k \cdot t^n + b \quad \text{(V)}$$

where Q is the amount released at the time t, $Q_\alpha$ is the overall released amount, k is a release rate constant of the nth order, n is a dimensionless number related to the dissolution mechanism and b is the y axis intercept, characterizing the initial burst effect. A value of n=0.5 characterizes a release mechanism controlled by polymer diffusion, while a value of n=1.0 characterizes an erosion controlled mechanism. Erosion and diffusion control the process in equal parts if n=0.66. Since the release rate constant k has the dimension hr$^{-n}$, values for different mechanisms cannot be compared directly. To overcome this problem it is possible to define another quantity termed the mean dissolution time (MDT). The MDT is the sum of the different periods of time the poloxamer molecules stay in the matrix before release, divided by the total number of molecules, and is calculated according to equation VI:

$$MDT = \frac{nk^{-1/n}}{n} \quad \text{(VI)}$$

Poloxamer 407 gels. in the absence of a membrane in the dissolution apparatus, exhibit erosion controlled kinetics (n=1.0) with an MDT of 1 hr. Placement of the cellulose ester membrane introduces a diffisional barrier to the release, and is characterized by equal contributions of erosion and diffusion control (n=0.66), with an MDT of 7 hr. Changes in gel viscosity (i.e. comparison of FloGel 25 vs. FloGel 28) and poloxamer fractionation do not 0 appreciably alter the dissolution mechanism or the MDT.

The addition of a modifier polymer, especially one of high molecular weight, can have profound effects on poloxamer dissolution. Cellulose ethers (e.g. CMC and HPMC) are long chain polymers. The solution characteristics appear to depend on the average chain length as well as the degree of substitution. As molecular weight increases, the viscosity will increase rapidly.

Addition of 0.5% w/w of the high viscosity CMC to a 25% w/w poloxamer 407 solution dramatically increases the MDT to 17 hr. It also changes the mechanism of release to one of pure diffusion control (i.e. n=0.50). Alternatively, the medium viscosity grade of CMC does not appear to have a dramatic effect on the MDT at the concentrations of modifier polymer employed. Other high molecular weight polymers (e.g. Carbopol 940-NF) also alter the dissolution mechanism and dramatically increase the MDT. In short it was suprisingly found that increases in the MDT by nearly an order of magnitude can be achieved by the addition of a modifier polymer. It is believed that the magnitude of the dissolution times measured in this in-vitro test are indicative of release rates found in-vivo in the peritoneal cavity.

EXAMPLE 4

Modification of the Gelation Temperature of Poloxamer Preparations Through the Incorporation of Hydrophilic Co-Surfactants In order to demonstrate the advantages associated with the addition of a hydrophilic co-surfactant to polymeric compositions in accordance with the present invention, several different preparations were formulated.

Methods.

Fractionated poloxamer 407 (i.e. poloxamer 407F) was prepared from NF grade Pluronic F-127 (BASF Corporation, Mount Olive, N.J.) as described herein. Hydrophilic co-surfactants in the form of fatty acid soaps (i.e. sodium oleate, sodium laurate, sodium caprate, and sodium caprylate) were obtained from Nu-Chek Prep. (Elysian, Minn.). The buffer materials, tromethamine (EM Sciences Inc., Gibbstown, N.J.) and maleic acid (Sigma Chemical Co., St. Louis, Mo.), were used as received, and a hypoosmotic buffer containing 0.1515% w/w tromethamine and 0.1451% w/w maleic acid was prepared. Final formulations contained a constant 20% w/w percentage of poloxamer 407F, and varying levels of fatty acid soaps.

For phase behavior studies, samples were loaded into 5 ml Wheaton vacuoles (Fisher Scientific, Pittsburgh, Pa.), and flame-sealed. The vacuoles were then immersed in a constant temperature bath. For temperatures less than 60° C., phase behavior was determined in a water bath (Koehler, Bohemia, N.Y.). At higher temperatures an oil bath (Haake, model DC3, Germany) was utilized. Temperature was raised in two degree increments from ca. 1° C. to 120° C. Samples were allowed to equilibrate for at least 1 hour at constant temperature prior to examination. Since the cubic liquid crystalline phase is isotropic (i.e. not birefringent), the determination of the gel boundary is somewhat subjective. Once equilibrium was reached, the vials were simply inverted and gravity was allowed to determine if the sample was in the sol or gel state.

Rheological studies were performed on a Rheometric Scientific Inc. (Piscataway, N.J.) model SR 5000 constant stress rheometer. A 25 mm parallel plate geometry with a gap of 1.0 mm was employed. In dynamic temperature ramp studies, a sinusoidal stress ($\omega$=1 s$^{-1}$) was applied at a stress less than the yield stress of the material (ca. 1–10 Pa). This ensured that the sample was in the linear viscoelastic region. Temperature was ramped at a rate of 2° C. min$^{-1}$. Rapid temperature equilibration was ensured with a peltier/water bath system. Samples were loaded at 0–5° C. (i.e. in the sol phase), and allowed to gel on the plate. This was done to avoid applying an unknown shear history to the sample. Plots of the complex viscosity ($\eta^*$) vs. temperature were recorded.

Discussion:

Details regarding the equilibrium phase behavior of 20% poloxamer 407F solutions with added fatty acid soaps are shown in Table III below. As may be seen from the data, fatty acid soaps have a substantial effect on the phase behavior of the poloxamer 407F solutions. The LGT for a 20% poloxamer 407F solution in the absence of added fatty acid soaps is 19° C. With added fatty acid soaps, the LGT can be increased to temperatures as high as 87° C. (observed with 4.86% added sodium caprate). In addition, the cloud point temperature, which is 108° C. for the 20% poloxamer 407F solution, may be easily increased to temperatures above 140° C., i.e. significantly above the typical temperatures used during terminal steam sterilization.

TABLE III

Phase behavior of 20% poloxamer 407F solutions in hypoosmotic tromethamine/maleate buffer with added fatty acid soaps.

| Concentration of Co-Surfactant (% w/w) | LGT (° C.) | UGT (° C.) | Cloud Point (° C.) |
|---|---|---|---|
| 0% Fatty Acid Soap | 19 | 81 | 108 |
| 1.0% Oleate (18:1) | 17 | 78 | 106 |
| 3.01% Oleate | 41 | 77 | 117 |
| 1% Laurate (12:0) | 22 | 78 | 110 |
| 1.5% Laurate | 31 | 84 | 114 |
| 2.0% Laurate | 49.5 | 84 | 121 |
| 2.2% Laurate | 54.5 | 83 | >140 |
| 2.4% Laurate | 57 | 77 | >140 |
| 2.5% Laurate | no gel | no gel | >140 |
| 1% Caprate (10:0) | 19.5 | 80 | 112 |
| 1.5% Caprate | 25 | 85 | 120 |
| 2.0% Caprate | 33 | 89 | 128 |
| 2.5% Caprate | 39.5 | 93 | 130 |
| 3% Caprate | 52 | 94 | >140 |
| 3.3% Caprate | 55 | 98 | >140 |
| 4.0% Caprate | 69.5 | 102 | >140 |
| 4.5% Caprate | 85 | 102 | >140 |
| 4.86% Caprate | 87 | 92 | >140 |
| 5% Caprate | no gel | no gel | >140 |
| 1% Caprylate (8:0) | 17.4 | 82 | 113 |
| 3% Caprylate | 19.5 | 94 | 131 |
| 4% Caprylate | 24.8 | 102 | >140 |
| 5% Caprylate | 34 | 109 | >140 |
| 5.5% Caprylate | 36 | 113 | >140 |
| 6.2% Caprylate | 43 | 120 | >140 |
| 8% Caprylate | 57.9 | >140 | >140 |
| 10% Caprylate | 74 | >140 | >140 |
| 10.57% Caprylate | 75 | — | >140 |
| 11.05% Caprylate | 75 | 150 | >150 |
| 11.48% Caprylate | no gel | no gel | >150 |

Figure 2:
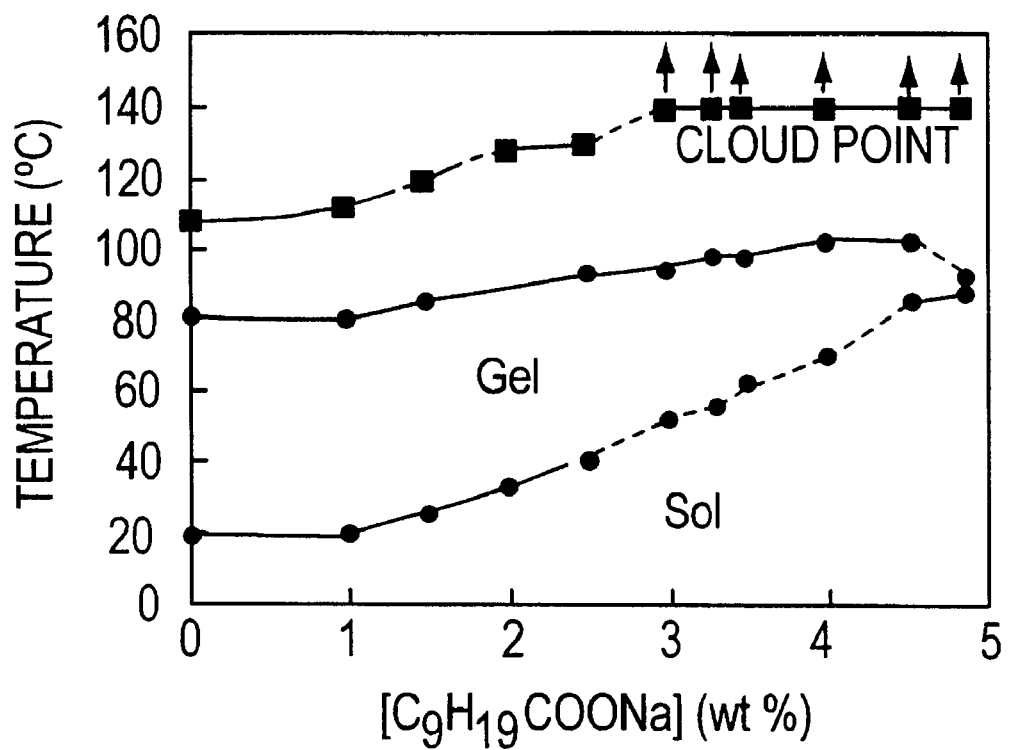
FIG. 2 illustrates an equilibrium phase diagram of 20% w/w poloxamer 407 (407F) in tromethamine/maleate buffer with added sodium caprate with arrows indicating that the cloud point temperature is greater than the highest temperature measured, i.e. 140° C.

In accordance with the results reported above a typical phase diagram obtained for poloxamer 407F/fatty acid soap mixtures is shown in FIG. 2. This diagram illustrates the effect of increasing sodium caprate concentrations on the phase behavior of 20% w/w poloxamer 407F solutions in the hypo-osmotic tromethamine/maleate buffer system.

Above a sodium caprate concentration of ca. 1% w/w, the LGT is observed to increase systematically from 19° C. to 87° C. At concentrations between ca. 1.5 and 2.0% caprate, the LGT is in the temperature range between room and body temperature. Having a LGT in this temperature range might have some importance for the formulation of antiadhesion products, possibly improving the ease of use by obviating the need to maintain product temperature near 0° C., and allowing the surgeon greater time to apply compositions in accordance with the methods herein. Above ca. 5% caprate, the gel phase is completely suppressed. Also of note in FIG. 2 is the fact that above ca. 2% sodium caparate, the cloud point temperature is above typical steam sterilization temperatures. Being able to maintain a single phase above terminal sterilization temperatures may play a role in reducing post-sterilization syneresis.

Figure 3:
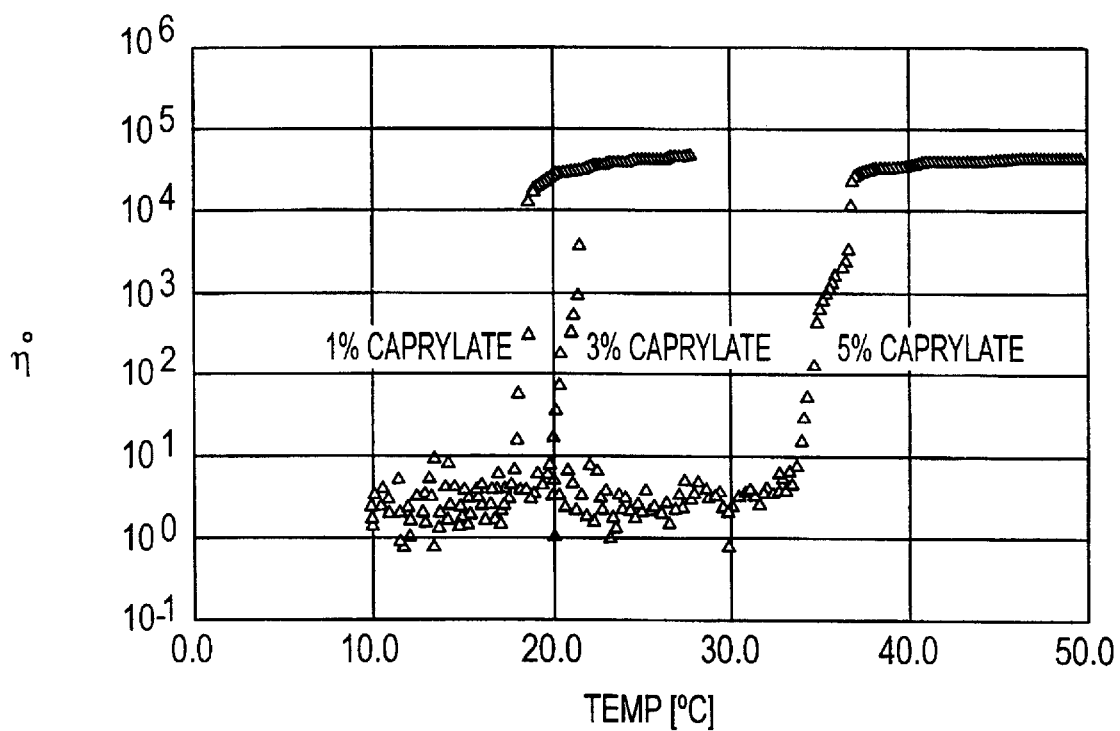
FIG. 3 is a graphical representation of a gelation profile of 1%, 3% and 5% (w/w) sodium caprylate in 20% w/w poloxamer 407 (407F) in hypotonic tromethamine/maleic acid buffer.

Dynamic temperature ramp studies for formulations with varying levels of added sodium caprylate are shown in FIG. 3. At low temperatures (below gel phase formation), the dynamic Theological method is not an efficient method for measuring low viscosities. This leads to a significant degree of noise in the data. Once the sol-gel phase transition is encountered, a sharp increase by ca. 4 orders of magnitude in the complex viscosity is noted. Above the phase transition, the dynamic rheological method is very sensitive and little noise is apparent in the data. Interestingly, the complex viscosity of the gel phase remains virtually constant as the LGT is varied by the addition of the hydrophilic co-surfactants. This is consistent with the model that the gel phase formation is due to the formation of a cubic array of micelles above their critical packing volume fraction. Accordingly, as long as the critical volume fraction is exceeded, the Theological properties of the gel do not appear to be significantly altered. Thus, the addition of fatty acid soaps represents a very efficient way of altering the LGT and cloud point of constitutive polymer gels without varying the rheological characteristics of the gel. This is, of course, in contrast to changing the LGT by varying poloxamer concentration, or the nature of the poloxamer (e.g. poloxamer 338).

Figure 4:
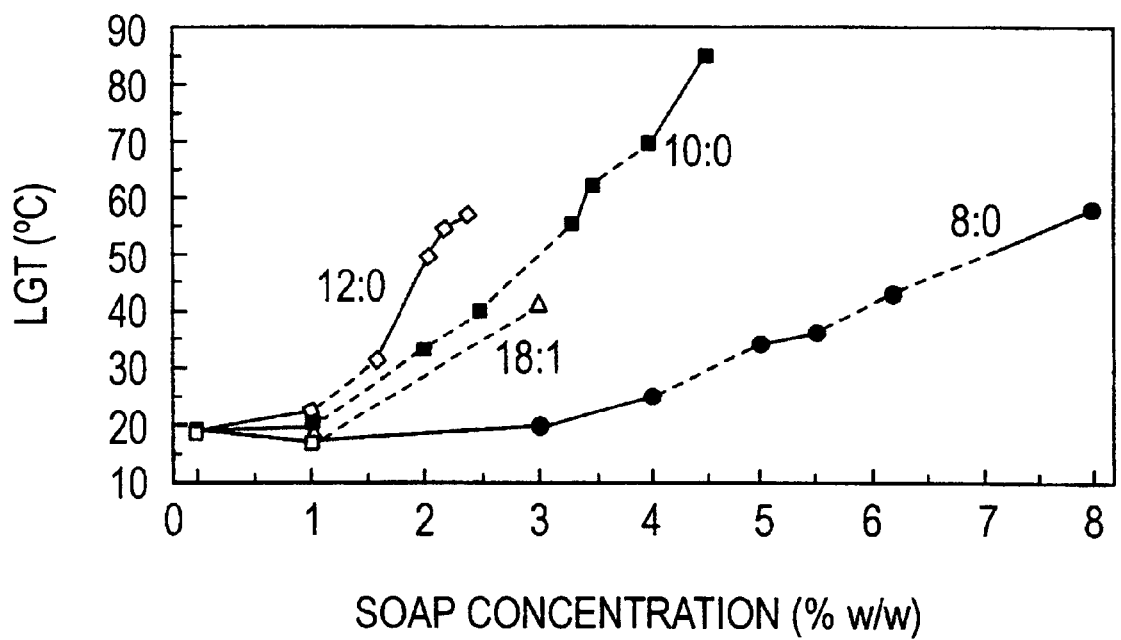
FIG. 4 is a graphical representation illustrating the effect of fatty acid soap concentration on the lower gelation temperature (LGT) of 20% w/w poloxamer 407F solutions for soaps of varying alkyl chain lengths and degrees of saturation.

The chainlength and degree of unsaturation of the hydrophilic co-surfactant may also be used to selectively alter the characteristics of the constitutive polymer gels. These effects are graphically illustrated in FIG. 4 where the LGT is plotted as a function of soap concentration for different fatty acid soaps. The value next to the curve refers to the fatty acid portion of the soap. Thus, 8:0 represents an eight carbon fatty acid soap with no double bonds in the alkyl chain. 18:1, on the other hand, represents an alkyl chain containing eighteen carbons and a single double bond. It is apparent from FIG. 4 that longer chainlength saturated soaps provide more substantial alterations of the gel characteristics than shorter chainlength analogues which appear to be less efficient at disrupting gel phase formation. Thus, while 2.5% of 12:0 soap is required to melt the 20% poloxamer 407F gel, nearly 11.5% of the 8:0 soap is used to provide the same characteristics. Unsaturated soaps also appear to be less active than their saturated analogues at increasing both the LGT and cloud point of poloxamer 407 gels. In any case, with a 20% w/w concentration of poloxamer 407F, it is possible to achieve gelation between room and body temperature, and a cloud point greater than 121° C. for the caprate (10:0) and caprylate (8:0) soaps. Moreover, as the total poloxamer concentration is increased, higher concentrations of hydrophilic co-surfactant may be used to achieve the same degree of shift in the LGT. Thus, the laurate soap (12:0) may be preferred under these conditions.

EXAMPLE 5

Drug Solubility and in-vitro Drug Release Rates in Poloxamer 407-Based Thermoreversible Gels In order to demonstrate the advantages of the present invention with respect to drug delivery, selected compounds were incorporated in various preparations formed in conjunction with the present invention.

Materials

The chemicals utilized in this study and their sources are listed below. All chemicals were used without further purification.

Ketoprofen (Sigma Chemical Co., St. Louis, Mo.)
Prednisone (Sigma Chemical Co., St. Louis, Mo.)
Indomethacin (Sigma Chemical Co., St. Louis, Mo.)
Tolmetin Sodium (Sigma Chemical Co., St. Louis, Mo.)
Hydrocortisone (Sigma Chemical Co., St. Louis, Mo.)
Poloxamer 407 (BASF, Mount Olive, N.J.)
Ethyl Alcohol 200 proof (Spectrum Chemical Co. Gardena, Calif.)
FloGel 28 (MDV Technologies Inc., Dearborn Mich.)

FloGel 25B/0.5C (MDV Technologies Inc., Dearborn Mich.)
FloGel 25 B/ 1 C (Alliance Pharmaceutical lot # 587-29b).
FloGel 25 (Alliance Pharmaceutical lot #587-29a).
FloGel 28F (Alliance Pharmaceutical lot #534-73).
Gentamicin Sulfate (Amresco, Solon, Ohio)

Methods

Preparation of Drug Solutions in Poloxamer 407-Water Systems.

Poloxamer 407 was added to deionized (DI) water in an ice bath (T=3–5° C.), and mixed until the poloxamer dissolved.

Excess amounts of drug were then added to the aqueous poloxamer solutions and allowed to equilibrate overnight (T=3–5° C.). The next day the sample was warmed momentarily to 40° C. to hasten solubilization. This process was repeated two or three times to ensure saturation. Samples containing less than 20% poloxamer 407 were then equilibrated overnight at room temperature while the other samples were equilibrated at 5°. Prior to analysis, the samples were filtered through a 0.2 μm nylon filter syringe to remove unsolubilized drug. Samples were assayed for solubilized drug concentrations by absorbance spectroscopy (see below).

Preparation of Drug Solutions in FloGel.

Two mg of drug was added to 1 mL of the FloGel material and equilibrated overnight (T=3–5° C.). As before, the sample was warned two to three times to 40° to hasten solubilization. Samples were stored at 5° C. until use.

Drug Concentration Determinations:

The samples were diluted to a suitable concentration with ethanol (for water insoluble drugs) or DI water. Drug concentrations were measured at the appropriate wavelength for each drug (see Table 1) using a UV/Vis spectrophotometer (Beckman model DU-65). Concentrations were determined using Beer's law from the appropriate calibration curve (Table II). Gentamicin sulfate determination was performed by the UCSD Medical Center laboratory.

In-vitro Release Rate of Drugs in Poloxamer Gels.

The in-vitro release rates of drugs in poloxamer-based gels were determined using a modified USP dissolution apparatus (Hanson Research model SR6) equipped with enhancer cells. Each of the dissolution vessels was filled with 25 mL of 0.01 M phosphate buffer (pH 7.4)[1] and left to equilibrate for about 20 minutes to 36.8° C. Membranes (1.2 μm cellulose ester membranes, 25 mm diameter, type RAWP) were presoaked in phosphate buffer and placed on the cell. Approximately 0.6 mL of sample in the fluid sol phase was then loaded into each of the enhancer cells. The cells were subsequently closed and the gel phase was allowed to form at room temperature prior to introduction into the dissolution vessels. The dissolution paddles were rotated at a speed of 100 rpm (approximating the hydrodynamic stress found at the peritoneal cavity) and were positioned approximately 1 cm from the top of the cells for all experiments. The in-vitro release of drug from the gels was monitored over a period of 4 hr. One mL samples were collected every 0.5 hr. The vessel was refilled with fresh buffer every time a sample aliquot was removed, and each sample was run in duplicate. For additional details regarding the dissolution apparatus the reader is referred to: (Dellamary L:In-vitro dissolution rates of poloxamer-based thermoreversible gels. *Research & Development Technical Report No. EPR*-32-97-4).

[1] 26.78 g of sodium phosphate dibasic (Na$_2$HPO$_4$7 H$_2$O) was brought to a volume of 1 L with DI water. The pH was adjusted to a pH of 7.4 with 1N HCl using a Sentron pH meter.

TABLE IV

Calibration Curve Equations for the Different Drugs Selected

| Drug | Calibration Curve Equation | R$^2$ |
| --- | --- | --- |
| Ketoprofen | Conc$_{mg/L}$ = 22.9(Abs) − 0.2 | 0.9996 |
| Prednisone | Conc$_{mg/L}$ = 33.3(Abs) − 0.06 | 0.9999 |
| Indomethacin | Conc$_{mg/L}$ = 232.4(Abs) − 2 | 0.991 |
| Tolmetin Sodium | Conc$_{mg/L}$ = 22.9(Abs) − 0.7 | 0.9919 |
| Hydrocortisone | Conc$_{mg/L}$ = 27.8(Abs) − 0.1 | 0.9956 | solubilization was, for most of the cases, enhanced in the gel state. Solubilization for hydrocortisone was higher in the liquid state. Two reasons could be responsible for the observed reduction in solubilization: 1) hydrocortisone has a relatively higher water solubility than the rest of the hydrophobic drugs tested: 2) samples below the gel transition temperature were equilibrated at room temperature, instead of the lower temperature used for the gels.

Apparent distribution coefficients ($K_m$) of the hydrophobic drugs between a micellar phase and an aqueous phase were determined according to equation VII.

$$\frac{S}{S_o} = K_m C + 1 \qquad (VII)$$

Where S and $S_O$ are the concentration of solubilized drug in the presence and absence of poloxamer, respectively. C is the concentration of poloxamer (weight fraction).

Table V, shows the apparent distribution coefficients. The higher the value of K, the greater the amount of drug that can be incorporated into the system.

TABLE V

Distribution Coefficients of Hydrophobic Drugs Between a Micellar Phase and an Aqueous Phase

| | Distribution Coeffiecient (log K$_m$) | |
| --- | --- | --- |
| Drug Evaluation | Liquid State | Gel State |
| Hydrocortisone | 1 | 0.55 |
| Prednisone | 1.1 | 1.5 |
| Ketoprofen | 2.9 | 3.1 |
| Indomethacin | 3 | 3.4 |

Positive distribution coefficients (log $K_m$) indicate that the drug preferably partitions into the micelle rather than into the water phase. Sodium tolmetin, in contrast, would rather partition into the water phase. It is not possible to calculate a partition coefficient for tolmetin using equation VII. The decreasing solubility with increasing poloxamer concentration gives a negative slope and an undefined value of log $K_m$. It is clear that tolmetin partitions almost entirely into the bulk aqueous phase and very little is solubilized in the poloxamer micelle. The above results confirm that hydrophobic drugs are actually solubilizing into the core of poloxamer 407 micelles.

There were no appreciable differences in diffusion coefficients or mean dissolution times (MDT) between different drugs within the same poloxamer formulations. Thus, no differences were observed between sodium tolmetin and ketoprofen despite the fact that the tolmetin is simply dissolved in the continuous aqueous phase of the gel while the ketoprofen is solubilized in the micelle core. These results imply that the micelles present little impediment to diffusion (i.e. there is no diffusional resistance). Significant reductions in the rate of diffusion are observed, however.

when a modifier polymer (i.e. carboxymethylcellulose, CMC) is added to the poloxamer.

The slow diffusion observed in poloxamer gets results (at least in part) from the longer diffusion path that a drug must take in order to pass around the micelles. In the case of polymer mixtures, the modifier polymer is preferably of sufficient molecular weight that it too alters the diffusion path of the solute. The fact that the size of the drug molecules did not seem to affect release rate also supports this hypothesis.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

What is claimed is:

1. A pharmaceutical aqueous-gel composition, said composition comprising a constitutive polymer selected from the group consisting of polyoxyalkylene block copolymers and polyoxyalkylene polyethers and combinations thereof, further including a modifier polymer selected from the group consisting of cellulose ethers, sodium carboxymethylcellulose and polyacrylates and further including a co-surfactant comprising at least one fatty acid soap.

2. The composition of claim 1 wherein said constitutive polymer is a polyoxyalkylene block copolymer of the formula:

$$Y[(A)_n\text{—}E\text{—}H]_x$$

wherein A is a polyoxyalkylene moiety;
x is at least 2;
Y is derived from water or an organic compound containing x hydrogen atoms;
E is a polyoxyethylene moiety;
n has a value such that the average molecular weight of A is at least about 500; and,
the total average molecular weight of the copolymer is at least about 5000.

3. The composition of claim 2 wherein A has an oxygen/carbon atom ratio of less than 0.5 and A is derived from an alkylene oxide selected from the group consisting of butylene oxide, propylene oxide or a mixture thereof.

4. The composition of claim 3 wherein A is a polyoxypropylene moiety and has an average molecular weight from about 3000 to 4000 g/mol.

5. The composition of claim 3 wherein the polyoxyethylene moiety E constitutes from about 60% to about 85% by weight of the copolymer.

6. The composition of claim 1 wherein the modifier polymer has a molecular weight greater than or equal to 500,000.

7. The composition of claim 1 wherein the modifier polymer has a molecular weight greater than or equal to 50,000.

8. The composition of claim 1 wherein the modifier polymer is incorporated in a range of between about 0.05% and about 25% by weight of the composition.

9. The composition of claim 8 wherein the modifier polymer is incorporated in a range between about 0.5% and about 5% by weight of the composition.

10. The composition of claim 1 wherein the constitutive polymer is in a concentration of about 2 to about 50 percent by weight of the composition.

11. The composition of claim 10 wherein the constitutive polymer is in a concentration of about 16 to about 28 percent of the composition.

12. The composition of claim 1 wherein said at least one fatty acid soap is selected from the group consisting of sodium oleate, sodium laurate, sodium caprate or sodium caprylate.

13. The composition of claim 1 comprising from about 0.05 to about 25 percent by weight of fatty acid soap.

14. The composition of claim 1 further including a bioactive agent.

15. The composition of claim 1 wherein said composition is used for reducing post-surgical adhesions.

16. The composition of claim 14 wherein the bioactive agent is selected from the group consisting of antibiotics, antivirals, mydriatics, antiglaucomas, anti-inflammatories, antihistaminics, antineoplastics, anesthetics, opthalmic agents, enzymes, cardiovascular agents, polynucleotides, genetic material, viral vectors, immunoactive agents, imaging agents, immunosuppressive agents, peptides, proteins physiological gases, gastrointestinal agents, humectants, bactericides, bacteriostatic agents, fibrinolytic agents or agents effective in preventing leukocyte migration into the area of surgical injury.

17. The composition of claim 16 wherein said composition is used for drug delivery.

18. A pharmaceutical aqueous-gel composition, said composition comprising constitutive polymers of the formula:

$$(R)_2N\text{—}(CH_2)_2\text{—}N(R)_2$$

wherein R is $H(OC_2H_4)_b(OC_3H_6)_a$— and a and b are integers such that the hydrophobic base represented by $(C_3H_6O)_a$ has a sum average molecular weight of at least about 2000, said composition further including a modifier polymer selected from the group comprising cellulose ethers, sodium carboxymethylcellulose and polyacrylates and further including a co-surfactant comprising at least one fatty acid soap.

19. The composition of claim 18 wherein the modifier polymer has a molecular weight greater than or equal to 500,000.

20. The composition of claim 18 wherein the modifier polymer is incorporated in a range of between about 0.05 to about 25 percent by weight of the composition.

21. The composition of claim 18 wherein the modifier polymer is incorporated in a range between about 0.5 and about 5 percent by weight of the composition.

22. The composition of claim 18 wherein the constitutive polymer is present in an amount of about 2 to about 50 percent by weight of the composition.

23. The composition of claim 18 wherein said fatty acid soap is selected from the group consisting of sodium oleate, sodium laureate, sodium caprate or sodium caprylate.

24. The composition of claim 18 comprising from about 0.05 to about 25 percent by weight of fatty acid soap.

25. The composition of claim 18 wherein the said composition is used for reducing post-surgical adhesions.

26. The composition of claim 18 further including a bioactive agent.

27. The composition of claim 26 wherein the bioactive agent is selected from the group consisting of antibiotics, antivirals, mydriatics, antiglaucomas, anti-inflammatories, antihistaminics, antineoplastics, anesthetics, opthalmic agents, enzymes, cardiovascular agents, polynucleotides, genetic material, viral vectors, immunoactive agents, imaging agents, immunosuppressive agents, peptides, proteins, physiological gases, gastrointestinal agents, humectants, bactericides, bacteriostatic agents, fibrinolytic agents or agents effective in preventing leukocyte migration into the area of surgical injury.

28. The composition of claim 27 wherein the said composition is used for drug delivery.

* * * * *